US 11,324,433 B2

(12) United States Patent
Zeng et al.

(10) Patent No.: US 11,324,433 B2
(45) Date of Patent: *May 10, 2022

(54) NON-LOCAL MEAN FILTERING FOR ELECTROPHYSIOLOGICAL SIGNALS

(71) Applicant: CARDIOINSIGHT TECHNOLOGIES, INC., Independence, OH (US)

(72) Inventors: Qingguo Zeng, Solon, OH (US); Venkatesh Vasudevan, Beachwood, OH (US); Charulatha Ramanathan, Solon, OH (US); Ping Jia, Solon, OH (US)

(73) Assignee: CARDIOINSIGHT TECHNOLOGIES, INC., Independence, OH (US)

( * ) Notice: Subject to any disclaimer, the term of this patent is extended or adjusted under 35 U.S.C. 154(b) by 945 days.

This patent is subject to a terminal disclaimer.

(21) Appl. No.: 15/965,295

(22) Filed: Apr. 27, 2018

(65) Prior Publication Data

US 2018/0242873 A1 Aug. 30, 2018

Related U.S. Application Data

(62) Division of application No. 14/158,021, filed on Jan. 17, 2014, now Pat. No. 9,974,458.

(60) Provisional application No. 61/753,803, filed on Jan. 17, 2013.

(51) Int. Cl.
| | | |
|---|---|---|
| *A61B 5/316* | (2021.01) | |
| *A61B 5/00* | (2006.01) | |
| *A61B 5/30* | (2021.01) | |

(52) U.S. Cl.
CPC ............... *A61B 5/316* (2021.01); *A61B 5/30* (2021.01); *A61B 5/7203* (2013.01)

(58) Field of Classification Search
None
See application file for complete search history.

(56) References Cited

U.S. PATENT DOCUMENTS

| | | |
|---|---|---|
| 2004/0230105 A1 | 11/2004 | Geva et al. |
| 2008/0300496 A1 | 12/2008 | Lee et al. |

FOREIGN PATENT DOCUMENTS

| | | |
|---|---|---|
| CN | 1479587 A | 3/2004 |
| CN | 102048531 A | 5/2011 |
| JP | 2007535345 A | 12/2007 |
| WO | 2003057025 | 7/2003 |
| WO | 2012092016 | 7/2012 |

OTHER PUBLICATIONS

Applicant-filed remarks in U.S. Appl. No. 14/158,021, pp. 9-21, filed Oct. 26, 2017.*
Thakor N V, et al., "Applications of Adaptive Filtering to ECG Analysis: Noise Cancellation and Arrythmia Detection", IEEE Transactions on Biomedical Engineering, IEEE Service Center, vol. 38, No. 8, Aug. 1, 1991, pp. 785-794.
Brian H. Tracey, et al., "Nonlocal Means Denoising of ECG Signals", IEEE Transactions on Biomedical Engineering, IEEE Service Center, vol. 59, No. 9, Sep. 1, 2012, pp. 2383-2386.
B.S. Moon, et al. , "Fuzzy Systems to Process ECG and EEG Signals for Quantification of the Mental Workload", Information Sciences, Jan. 1, 2002, pp. 23-35.
Singer, et al. "Diffusion Interpretation of Nonlocal Neighborhood Filters for Signal Denoising", Society for Industrial and Applied Mathematics, 2009 [retrieved on Jun. 18, 2014]. Retrieved from the internet: URL:https://www.math.ucdavis.edu/~sailto/data/acha.read.s1/nadler-shkolnisky-singer-siamis.pdf entire document, pp. 118-139.
International PCT Application No. PCT/US2014/012040, International PCT Filing Date: Jan. 17, 2014; PCT International Search Report and Written Opinion; Authorized Officer: Blaine R. Copenheaver; dated Jul. 9, 2014; 9 pgs.
Chinese Application No. 201480010820.7; Filing Date: Jan. 17, 2014; Applicant: CardioInsight Technologies, Inc.; Chinese Office Action dated Feb. 12, 2018; 7pgs.
European Aplication No. EP14740726; Filing Date: Jan. 17, 2014; Applicant: CardioInsight Technologies, Inc. Supplementary European Search Report; Date of Completion: Jul. 12, 2016; 9 pgs.

* cited by examiner

*Primary Examiner* — G Steven Vanni
(74) *Attorney, Agent, or Firm* — Tarolli, Sundheim, Covell & Tummino LLP

(57) ABSTRACT

A method can include storing input electrical signal data representing at least a given electrophysiological signal acquired from a patient. A non-local mean filter can be applied to the given electrophysiological signal, the non-local mean filter including a spatial filter component and an intensity filter component. The method can also include controlling parameters to establish weighting of each of the spatial filter component and the intensity filter component in response to a control input. Filtered signal data can be stored based on the applying and the controlling.

20 Claims, 6 Drawing Sheets

NON-LOCAL MEAN FILTERING FOR ELECTROPHYSIOLOGICAL SIGNALS

CROSS-REFERENCE TO RELATED APPLICATIONS

This application is a divisional application of U.S. patent application Ser. No. 14/158,021 filed Jan. 17, 2014 and entitled NON-LOCAL MEAN FILTERING FOR ELECTROPHYSIOLOGICAL SIGNALS which claims the benefit of U.S. Provisional Patent Application No. 61/753,803 filed Jan. 17, 2013 and entitled NON-LOCAL MEAN FILTERING FOR PHYSIOLOGICAL SIGNALS, each of which is incorporated herein by reference in its entirety.

TECHNICAL FIELD

This disclosure relates to non-local mean filtering for electrophysiological signals.

BACKGROUND

Electrophysiological signals are sensed in a variety of applications, including electroencephalography, electrocardiography, electromyography, electrooculography and the like. In some applications, line filters may be incapable of removing noise caused by certain influencing factors, such as frequency shift and the like. Since most existing approaches utilize frequency based approach, for a selected small interval, artifacts from interval boundaries can contaminate the filtering results across the whole interval. This contamination tends to be more detrimental as the level of information being extracted from the signals increases.

SUMMARY

This disclosure relates to non-local mean filtering for electrophysiological signals.

In one example a non-transitory computer-readable medium having instructions executable by a processor, the instructions programmed to perform a method. The method can include applying a non-local mean filter to a given electrophysiological signal to provide a first recovered signal and a first residual signal. The method can also include applying the non-local mean filter to one of the first recovered signal and the first residual signal to provide a feature signal and a second residual signal. The method can also include combining the first recovered signal with the feature signal to provide a filtered version of the given electrophysiological signal.

As another example, a filter system can include a non-local mean filter comprising a spatial filter component and an intensity filter component configured to adaptively average neighboring samples in a neighborhood for each sample of a given electrophysiological signal. A filter control can be configured to set spatial parameter data to configure the spatial filter component according to a distance in a sampling space for the given electrophysiological signal and to set intensity parameter data to configure weighting of the intensity filter component according to an intensity difference between samples in the given electrophysiological signal.

As yet another example, a method can include storing input electrical signal data representing at least a given electrophysiological signal acquired from a patient. A non-local mean filter can be applied to the given electrophysiological signal, the non-local mean filter including a spatial filter component that provides spatial filtering in a spatial domain of the given electrophysiological signal according to a distance between each sample and its neighboring samples of the given electrophysiological signal. The filter can also include an intensity filter component to provide filtering in an intensity domain of the given electrophysiological signal according to an intensity difference between each sample and its neighboring samples of the given electrophysiological signal. The method can also include controlling parameters to establish weighting of each of the spatial filter component and the intensity filter component in response to a control input. Filtered signal data can be stored based on the applying and the controlling.

DETAILED DESCRIPTION

This disclosure relates to non-local mean (NLM) filtering that can be applied to reduce noise from sensed electrophysiological signals. As disclosed herein, NLM filtering can be referred to as an intensity-based approach to filtering physiological signals. An NLM filter can be configured to remove white noise (e.g., Gaussian noise), fixed frequency noise (e.g., power line noise) and/or transient noise (e.g., spike noise), for example.

As disclosed herein, systems and methods can identify and process electrophysiological signals for a given geometric surface based on application of non-local mean filtering applied to the signals. By way of example, the non-local mean filtering disclosed herein can be applied to signals reconstructed onto a geometric surface (e.g., an endocardial or epicardial surface) or otherwise derived from signal measurements. In other examples, the non-local mean filtering disclosed herein can be applied to electrophysiological signals measured directly from a surface of a patient's tissue.

By way of example, the systems and methods disclosed herein can be used as part of a diagnostic and/or treatment workflow to facilitate the identification and treatment of fibrillation mechanisms based on electrical activity acquired for the patient. In some examples, the patient electrical activity can include non-invasive body surface measurements of body surface electrical activity. Additionally or alternatively, the patient electrical activity can include invasive measurements of heart electrical activity, including epicardial measurements and/or endocardial measurements. While many examples herein are described in the context of cardiac electrical signals, it is to be understood that the approaches disclosed herein are equally applicable to other electrophysiological signals, such as electroencephalography, electromyography, electrooculography and the like.

Figure 1:
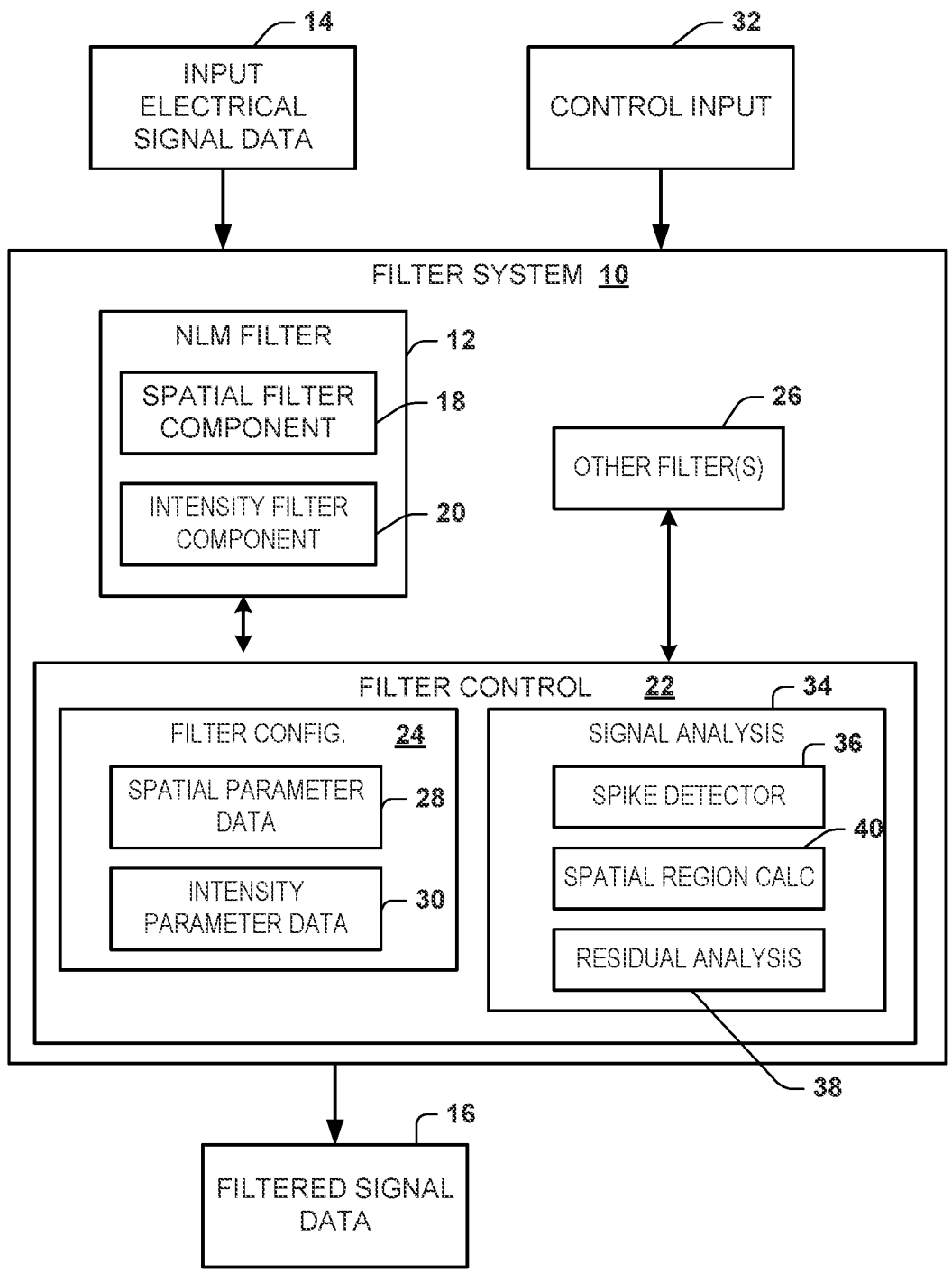
FIG. 1 depicts an example of an NLM filter system.

FIG. 1 depicts an example of a filter system 10 that can implement an NLM filter 12 for processing input electrical data 14. The input electrical data 14 can correspond to electrophysiological signals, such as can correspond to physiological signals obtained by one or more electrodes.

The electrodes can be applied to measure the electrical activity non-invasively, such as may be positioned over a patient's body surface such as the patient's head (e.g., for electroencephalography), a patient's thorax (e.g., for electrocardiography) or other noninvasive locations. In other examples, the input electrical data 14 can be acquired invasively, such as by one or more electrodes positioned within a patient's body (e.g., on a lead or a basket catheter during an EP study or the like). In yet other examples, the input electrical data 14 can include both non-invasively acquired electrical signals and invasively acquired electrical signals.

In some examples, prior to implementing the NLM filter 12, initial line filtering, such as low pass or other filtering, can be implemented on the raw signals to provide the corresponding input electrical data 14. Additional signal processing techniques can also be utilized to provide such input electrical data 14. As an example, the signal processing techniques can include electrogram reconstruction onto an epicardial or other envelope, such as by solving an inverse solution based on geometry data and electrical data measured over a body surface.

The NLM filter 12 is configured to adaptively average each of the input signals (e.g., provided by input electrical data 14) spatially and/or temporally in a neighborhood of each sample to filter noise and provide a filtered version of the input signal demonstrated as filtered signal data 16. The filter system 10 can be configured to apply filtering, including, but not limited to the NLM filter 12 to each input signal and provide corresponding filtered output signals in the filtered signal data 16. Such other filtering is demonstrated schematically as one or more other filters 26.

The NLM filter 12 can be configured to perform denoising by combining spatial information and intensity information provided in the input signal. As used herein, the spatial information can represent a geometric distance (e.g., a distance in a two-dimensional or three-dimensional geometry) and/or a temporal distance (e.g., a temporal distance between time indices for sample points of one or more signals). As demonstrated in FIG. 1, the NLM filter 12 includes a spatial filter component 18 and an intensity filter component 20. The spatial filter component 18 enables the NLM filter 12 to consider a spatial and/or temporal distance of points in a given signal. For example, the spatial filter component can be configured for weighting the filter applied to signal according to a relative temporal characteristic (e.g., an absolute time or a time difference) between a given sample point of such signal and other points in one or more signals. in a corresponding neighborhood of samples relative to the sampled point of the signal. Additionally or alternatively, the spatial filter component 18 can enable the NLM filter 12 to apply weighting in the filter according to a geometric distance (e.g., in a two-dimensional or three-dimensional geometry) between a location of a given signal and one or more other signals across a geometric surface. The intensity filter component 20 applies a weighting based on a relative magnitude of a sample point of the signal and the corresponding samples in the neighborhood of each sample point. Thus, the relative intensity and magnitude of the samples in the neighborhood are utilized to perform smoothing and denoise the input signal.

The NLM filter 12 is programmable for each input signal represented by the input electrical data 14 or for a selected portion of each respective signal based on setting one or more parameters. The programmable parameters can include parameters of the spatial filter component 18 and the intensity filter component 20. As mentioned above, each input electrical signal represented by the input electrical data 14 can represent electrical activity at a different spatial location across a geometric surface of patient tissue.

In order to configure the spatial filter component 18 and/or the intensity filter component 20, the filter system 10 includes a corresponding filter control 22. In the example of FIG. 1, the filter control 22 includes a filter configuration function 24 programmed to configure the NLM filter 12. The filter configuration function 24 can also be programmed to configure one or more other filters 26. The filter control 22 and configuration function can operate to configure the NLM filter 12 and/or other filters 26 in response to a control input 32, such as disclosed herein.

In the example of FIG. 1, the filter configuration function 24 can set spatial parameter data 28 and intensity parameter data 30 for configuring the spatial filter component 18 and the intensity filter component 20, respectively. By applying the spatial parameter data 28 and the intensity parameter data 30 to the NLM filter 12, the NLM filter can perform denoising and/or other filter operations based on both spatial distance and intensity difference in the input electrical signals represented by the input electrical data 14. In this context and in many examples disclosed herein, spatial parameter corresponds to a temporal distance associated with the input signal (e.g., a temporal distance), such that distance between a sample point and samples in a neighborhood of samples corresponds to a difference in time for each of the respective samples. In other examples, the spatial parameter can correspond to a geometric distance (e.g., two-dimensional or three-dimensional geometry of the spatial domain) between a given signal sampled at one location and one or more other signals at other locations of a geometric surface. As a result, the NLM filter can be configured differently for different applications depending on whether an increased weighting is desired for spatial and/or intensity filtering. For example, different spatial parameters can be utilized to control how the distance between neighboring samples is to be emphasized or de-emphasized when the filtering is applied. Additionally or alternatively, different intensity parameters (e.g., based on intensity differences) can be implemented to control the extent to which differences in magnitude are removed or kept in a given signal in response to NLM filtering.

As an example, the filter configuration function 24 can configure the spatial parameter data 28 and/or the intensity parameter data 30 according to a control input 32. The control input 32 can be set according to application requirements. For example, the control input 32 can be provided in response to a user input selecting a type of filtering that is to be implemented. In other examples, the control input 32 can be provided in response to the user input that selects the value for one or both of the spatial parameter data 28 and the intensity data parameter data 30. In still other examples, the control input 32 can be provided to set one or both of the spatial parameter data 28 and the intensity data parameter data 30 by another application or function (not shown) automatically, such as based on analysis of signal characteristics or other automated functions.

As a further example, the filter system 10 can provide a user interface through which a user can set one or both of the spatial and intensity parameters. Additionally or alternatively, the filter configuration function 24 can establish the size of a neighborhood of samples (e.g., a moving time window) that is used in the NLM filter 12. The neighborhood can be a fixed size neighborhood or it can be variable such as in response to the control input 32. The filter control 22 further can control application of the NLM filter 12 and its configuration depending upon application requirements for the filtering that is being implemented.

Additionally, the filter control 22 can apply one or more instances of the NLM filter 12 for processing a given input signal, which instances can be applied iteratively according to application requirements. For example, the filter control 22 can apply a given instance of the NLM filter 12 to an input signal to provide a filtered recovered signal and a residual signal corresponding to the portion of the signal that has been removed via the filtering by the NLM filter. The filter control 22 can in turn apply signal analysis 34 on the residual signal component to effectively recapture salient features from the residual that can be recaptured added back to the recovered signal to provide a corresponding denoised output signal that can be stored at the filtered signal data 16.

In some examples, the subsequent instances of the NLM filter 12 that are applied can be the same instance, namely, having the same spatial parameter data 28 and same intensity parameter data 30. In other examples, different filter parameters can be set by the filter control 22 based on the signal analysis 34 or based on a predefined application of the NLM filter 12 to adjust the spatial parameter data 28 and/or the intensity parameter data 30 for the subsequent application of the NLM filter on one or more signal components that have been generated by a preceding application of the NLM filter.

By way of further example, the signal analysis 34 can include one or more functions for analyzing the input signal that is being filtered and the filter configuration function 24 can apply the results of the analysis for setting the filter parameters 28 and 30. For example, the signal analysis 34 can include a spike detector 36 that is configured to identify the location (e.g., time) for one or more spikes that might exist in a given input signal (or a recovered or residual signal component). The location of the spikes can be provided to the filter configuration function 24 for applying different filter configuration parameters to a neighborhood centered at the detected spike location. The detected spike can correspond to a naturally occurring biological event (e.g., an arrhythmia, such a fibrillation) or the spike can be a pacing spike induced by a device, for example.

As another example, the signal analysis 34 can include a residual analysis function 38 that is configured to analyze the residual signal to determine if any salient features might exist in the residual signal that should be recaptured for insertion back into an associated recovered filter signal. The salient features can be a common characteristic across the residual signal or it can include different characteristics that can be identified by the analysis function 34 and recaptured through application of corresponding different NLM filters. For example, where one or more spikes might exist in a residual signal that should be recaptured for a given application, the filter configuration function 24 can employ the residual analysis 38 and spike detector 36 functions to set the intensity parameter data 30 with a relatively higher weight value than the spatial parameter data 28 to recover spikes from the residual signal and, in turn, add the detected spikes to the previously recovered signal.

In some examples, the application of the NLM filter can be applied to the entire input sample over a corresponding time interval. In other examples, the filter configuration function 24 can configure the NLM filter to be applied at one or more spatial (e.g., temporal) regions of the input sample, such as can be determined by a spatial region calculator 40 of the signal analysis function 34. For instance, the spatial region calculator 40 can specify a spatial region of interest relative to one or more salient signal features, such as a spatial region centered about a spike or other feature. As mentioned, the filter control 22 can apply one or more instances of the NLM filter 12 as part of an iterative process to denoise or otherwise filter the signal according to application requirements to provide the corresponding filtered signal data 16.

As a further example, the NLM filter 12 can be configured to adaptively average signals in a neighborhood of each sample to filter noise. For a given signal $S(i), i=1, \ldots, n$ that is contaminated by noise, the NLM filter can provide a smoothed result $\hat{S}(i)$ via $$\hat{S}(i) = \sum_{j \in N(i)} w(i, j) S(j), \qquad (1)$$

where $N(i)$ is neighborhood of the sample $S(i)$, and $w(i,j)$ is a weight factor applied on sample $S(j)$, satisfying $$\sum_{j \in N(i)} w(i, j) = 1. \qquad (2)$$

An example embodiment of the NLM filter 12 can be derived from a traditional type of Gaussian filter, which can be expressed as follows:

$$h_\sigma(i, j) = e^{-\frac{(i-j)^2}{2\sigma^2}} \qquad (3)$$

$$w(i, j) = \frac{h_\sigma(i, j)}{\sum_{k \in N(i)} h_\sigma(i, k)}. \qquad (4)$$

where $\sigma$ is the standard deviation for a Gaussian kernel. In the example of Gaussian smoothing, for each given sample to be smoothed, the impact of the neighboring samples is solely controlled according to a distance between the neighboring samples and the sample to be smoothed. This can make it difficult to keep sharp edges for such Gaussian smoothing.

The NLM filter 12 accounts for both spatial distance and intensity difference among neighboring samples, such as by expressing:

$$h_{\sigma_1,\sigma_2}(i, j) = e^{-\left(\frac{(i-j)^2}{2\sigma_1^2} + \frac{(s(i)-s(j))^2}{2\sigma_2^2}\right)}, \qquad (5)$$

where $\sigma_1$ and $\sigma_2$ represent standard deviations defined in spatial (e.g., temporal) domain and intensity domain, respectively.

The parameters $\sigma_1$ and $\sigma_2$ to can be adjusted according to application requirements, such as by the filter configuration function 24 setting the spatial parameter 28 and intensity parameter 30. For example, the spatial parameter 28 can represent a standard deviation $\sigma_1$ and the intensity parameter 30 can represent the standard deviation $\sigma_2$ as in equation (5). Additionally, the distance between a given sample i can its set of neighboring samples j can be determined as $(i-j)^2$, which distance can be weighted by $\sigma_1$, as shown in the example of equation (5), where i and j are times for the respective samples. Additionally, the difference between an intensity of a given sample $s(i)$ and the intensity of its set of neighboring samples s(j) can be determined for each of the samples, which difference can be weighted by $\sigma_2$, such as shown in the example of equation (5). As disclosed herein, the spatial and intensity parameters 28 and 30 can be set to fixed values or be programmable in response to the control input 32. The NLM filter 12 can also be applied multiple times to a given input signal based on different applications, which can include the same or different spatial and intensity parameters 28 and 30.

In some examples, to help improve performance, another type of weighting can be utilized for accounting for accounts for both spatial distance, such as $(i-j)^2$, and intensity difference, such as $(s(i)-s(j))^2$, among neighboring samples, such as according to the following expression:

$$h_{\sigma_1,\sigma_2}(i,j) = e^{-\frac{(i-j)^2}{2\sigma_1^2}} \frac{1}{1+\frac{(s(i)-s(j))^2}{\sigma_2^2}} \quad (6)$$

It is to be understood that, as disclosed herein, the spatial distance can correspond to a temporal distance and/or a geometric distance in the signals being filtered.

Figure 2:
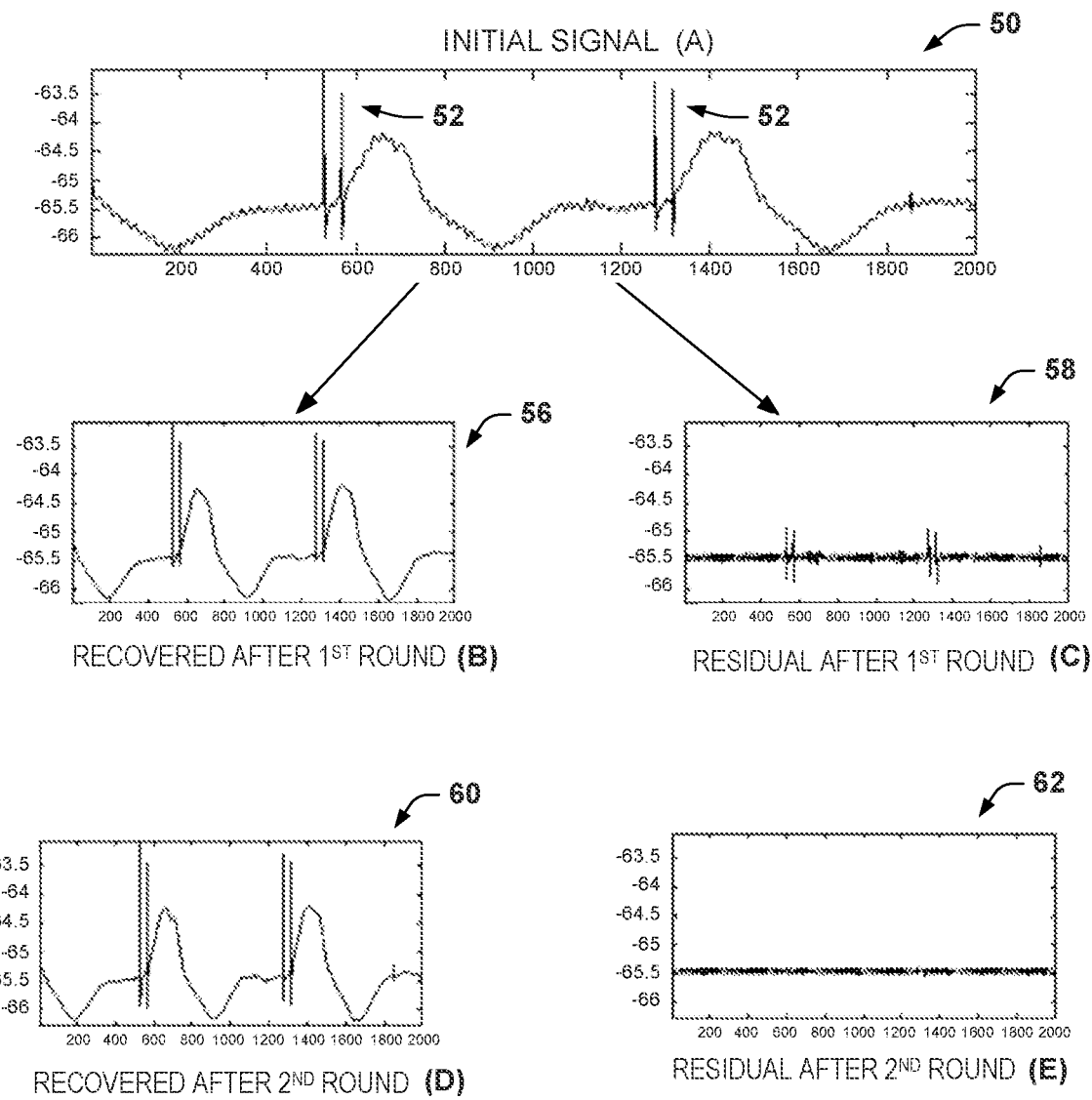
FIG. 2 depicts an example of noise reduction utilizing NLM filtering.

By way of example, FIG. 2 depicts an example of noise reduction that can be implemented by employing NLM filtering. As an example, the NLM filter 12 can be applied to the original noisy signal 50, such as can be configured with large $\sigma_1$ to allow effective average for neighboring samples, but keep $\sigma_2$ to be small to mitigate spikes in the resulting filtered signal. In the example of FIG. 2, an initial signal 50 is processed by an NLM filter 12, which application results in corresponding filtered signals 56, 58, 60 and 62, as shown therein. Letters (a), (b), (c), (d) and (e) are also utilized in the following description of FIG. 2 to refer to the signals 50, 56, 58, 60 and 62.

For instance, after a first application of the NLM filter 12, the original signal (a) can be represented by the following component parts:

(a)=(b)+(c)

where (a) is the original signal 50,
(b) is the denoised resulting recovered signal 56, and
(c) is the residual signal 58.

From the residual signal (c), it can be determined that there are one or more features that should not be removed. In this example, the same NLM filter 12 can further be applied to the residual signal 58 to provide a denoised version of (c). Based on application of the NLM filter 12 to the signal (c), the features and residual of the signal 58 can be expressed as:

(c)=(c)'+(e)

where (c)' is the feature extracted and (e) is the residue of (c).

From the foregoing, substituting for (c), the original signal 50 can be expressed as follows:

(a)=(b)+(c)=(b)+(c)'+(e).

The signal features of (b) and (c)' and thus be combined to provide (d). That is, (d)=(c)'+(b). Thus, in FIG. 2, the signal 60 includes the desired features of the original signal (a). Thus, absent other noise the original signal 50 can be expressed as:

(a)=(d)+(e).

Referring back to FIG. 1, the residual analysis 38 can be applied to determine that the residual signal 62 in FIG. 2 resulting from the second application of the NLM filter 12 does not show any salient feature. Accordingly, the signal 60 (demonstrated as (d)) can be treated as the final resulting signal that can be stored as filtered signal data 16 (FIG. 1).

Figure 3:
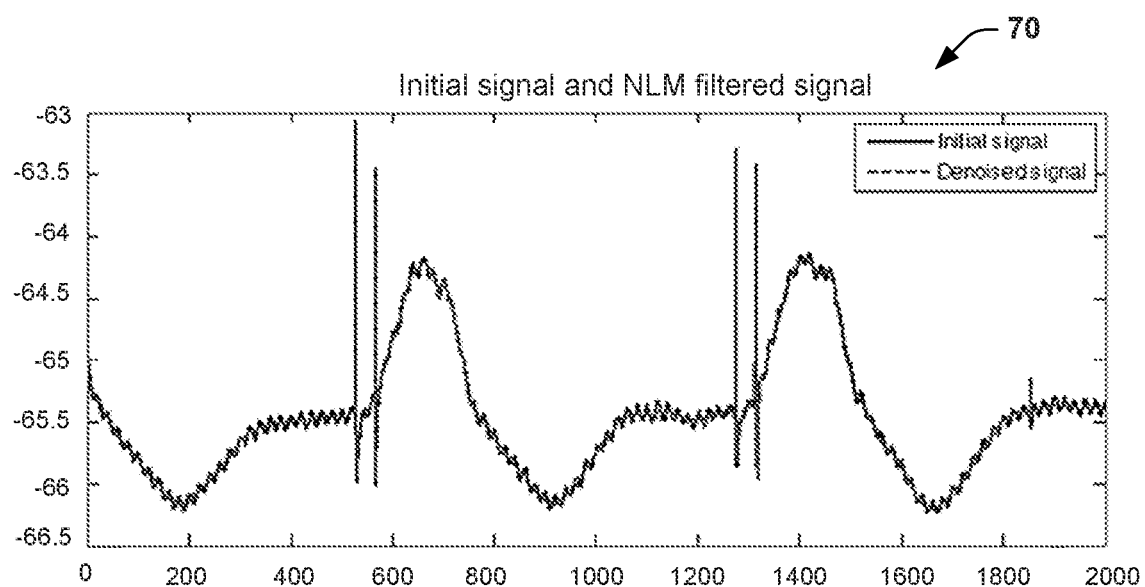
FIG. 3 demonstrates an example of denoised and original signals.

FIG. 3 is a plot 70 of both noisy and filtered signals demonstrating the effectiveness of a denoising NLM filter that can be implemented. As shown in FIG. 3, the plot 70 demonstrates overlapping noisy data with denoised results. Additionally, since the NLM filtering can be implemented as a purely an intensity based approach, it will not be affected by frequency changes in the noise. Thus, as disclosed herein, additional filtering 26 can be employed to remove frequency-based noise, if desired.

While the examples of FIGS. 2 and 3 demonstrate employing the NLM filter 12 configured for denoising an input signal, the NLM filter 12 can also be implemented to remove transient features (e.g., spikes) from electrophysiological (e.g., electrogram) signals. To remove spikes, for example, the NLM filter 12 can be configured, such as with reference to equation (6) with large $\sigma_1$ (e.g., spatial parameter 28) to allow effective average for neighboring samples and large $\sigma_2$ (e.g., magnitude parameter 30).

Figure 4:
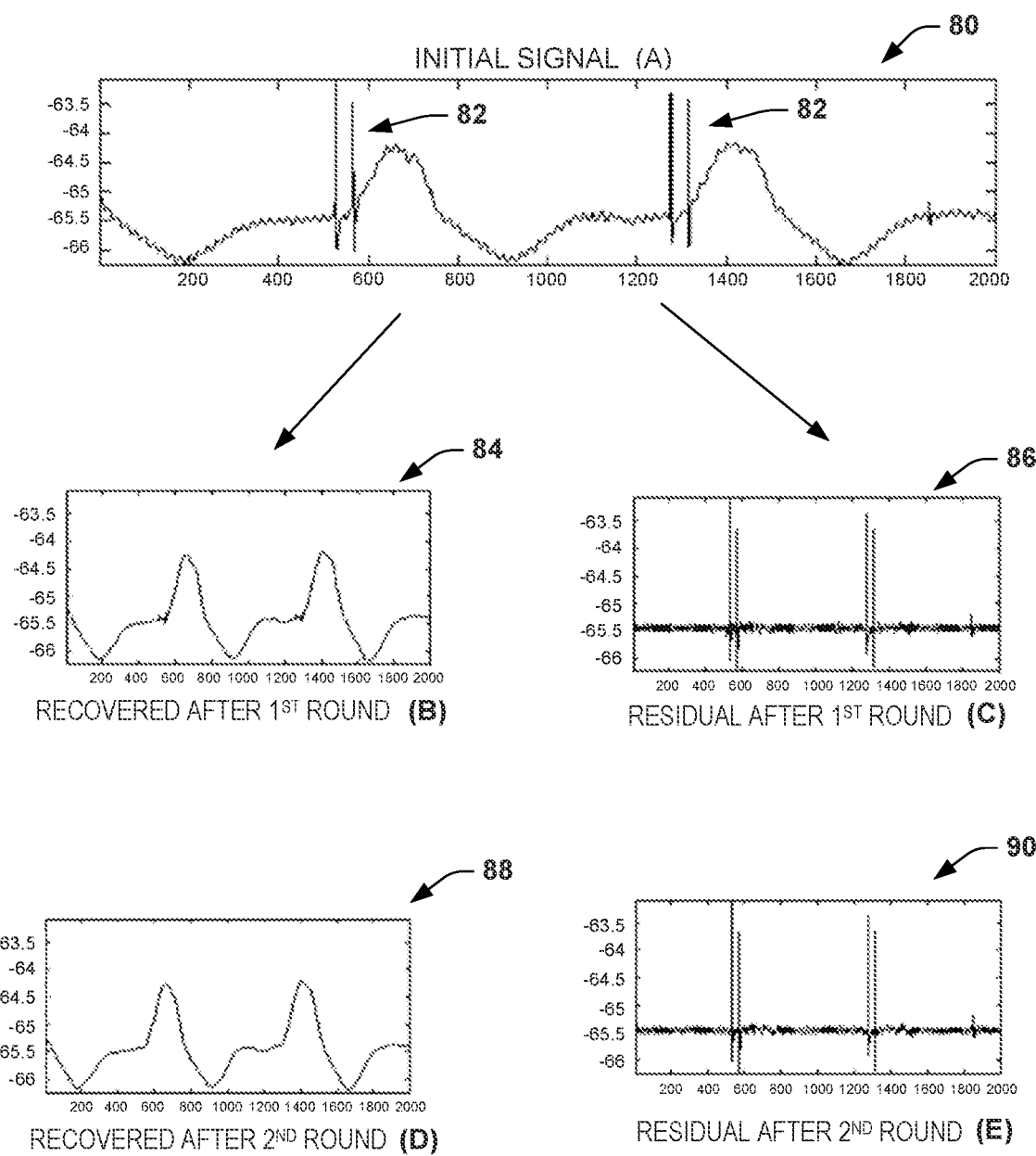
FIG. 4 depicts an example of spike removal.

FIG. 4 depicts an example of applying the NLM filter 12 configured to remove spikes. In the example of FIG. 4, an initial signal 80 includes spikes. The initial signal is process by the NLM filter 12 to provide a recovered signal 84 and a residual signal 86. Further processing by another iteration of the NLM filtering provides a recovered signal 88 and an aggregate residual signal 90. In the example of FIG. 4, the signals 80, 84, 86, 88 and 90 are also represented by letters (A), (B), (C), (D) and (E), respectively. Since the NLM filter 12 is being implemented to remove spike features from the electrophysiological signals, in this example, the workflow and application of the NLM filter in this approach differs somewhat from the approach applied in the noise reduction example of FIG. 2. Specifically, instead of applying NLM on the residual signal in the second iteration as in the example of FIG. 2, in the example of FIG. 4, the NLM filter 12 is applied on the recovered portion of the signal 84. The application of NLM on the recovered signal 84 results in a substantially spike free signal in the signal 88, with further spikes present in the residual 90.

Figure 5:
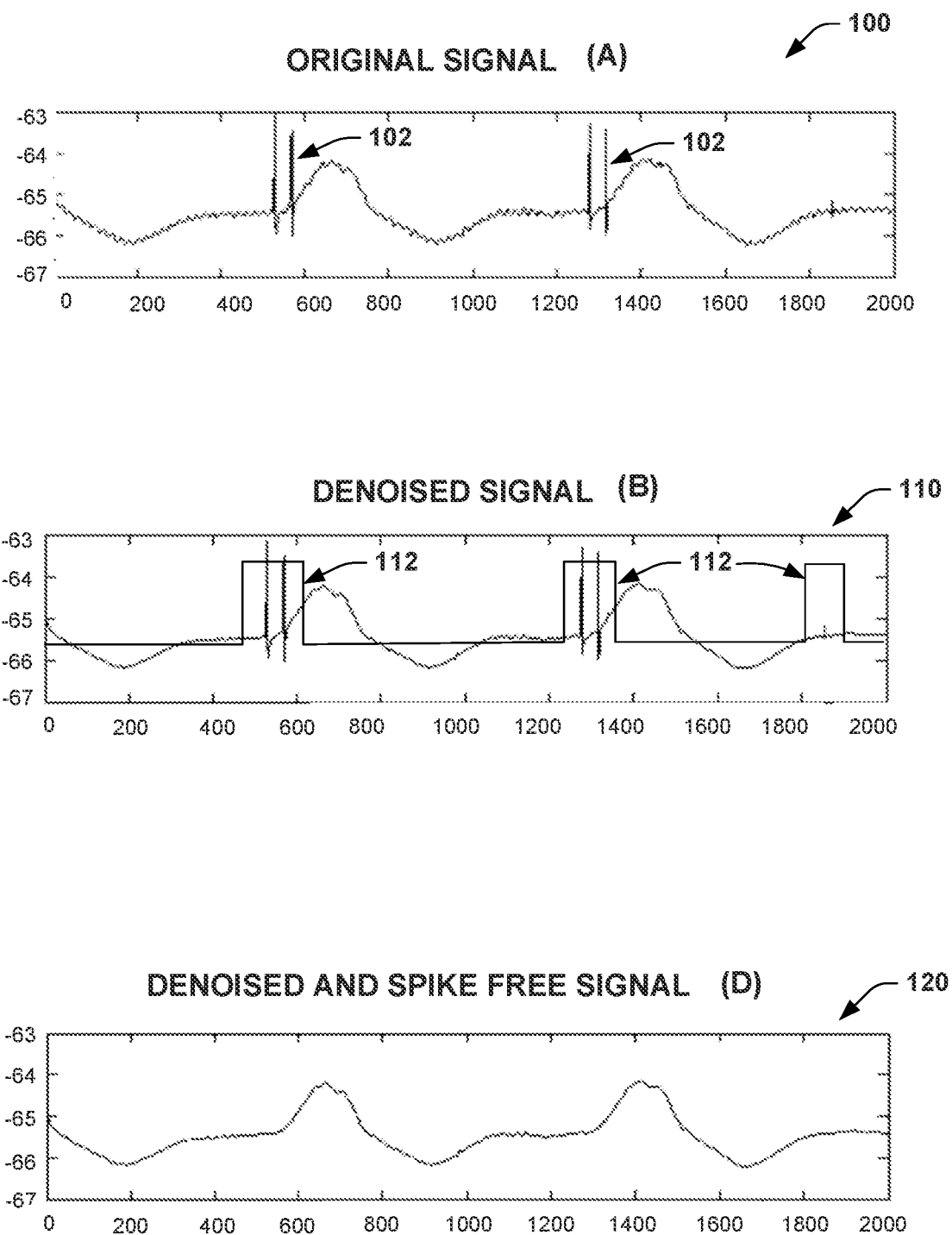
FIG. 5 depicts another example of spike removal.

A second example approach that can be implemented by the NLM filter 12 to mitigate transient signal features (e.g., spikes) is demonstrated in the example of FIG. 5. In this example, instead of applying filtering on every sample of an original signal, the filter control can selectively apply the NLM filter 12 to regions of the signal that have been identified (e.g., by spike detector 36 of FIG. 1) as containing spikes. As demonstrated in the example of FIG. 5, an original signal 100 (also referred to as signal (A) for consistency with FIGS. 2 and 4) includes spikes 102. The NLM filter 12 can be configured for denoising, such as disclosed with respect to FIG. 2, to recover a corresponding denoised signal 110 (also referred to as signal (B) for consistency with FIGS. 2 and 4). Regions in the denoised signal containing spikes can be identified by the spike detector of the signal analysis function. Corresponding time indices can be identified to set time windows 112 for each of the spikes in the denoised signal 110, such as demonstrated in the example of FIG. 5. The NLM filter 12 or another filter 26 can be configured to smooth the samples within each of the time windows 112 near each of the spike regions to provide a desired denoised and spike free signal (also referred to as signal (D) for consistency with FIGS. 2 and 4).

For example, various types of smoothing filter functions can be applied to the samples in the identified spike regions 112 (e.g., a Savitzky-Golay or other smoothing filter).

The approach demonstrated in FIG. 5 for performing spike removal can be implemented to mitigate over smoothing non-spike regions. Additionally, the approach in the example of FIG. 5 can require less processing resources (e.g., it can be faster to compute) since the smoothing filter is applied to selected parts for spike removal instead of the entire sample as in some other examples.

This disclosure provides some preliminary results of a new non-local mean filter, regarding its applications on denoising and spike removal. It can be applied on to electrophysiological data, such as including atrial fibrillation (AF) cases—especially on intervals without spreading artifacts at the beginning and end of chosen intervals.

The resulting denoised and/or de-spiked signals can also be further processed and utilized to generate a graphical visualization to present spatially and temporally consistent information in the one or more physiological graphical maps (e.g., presented according to a color scale or grayscale).

Figure 6:
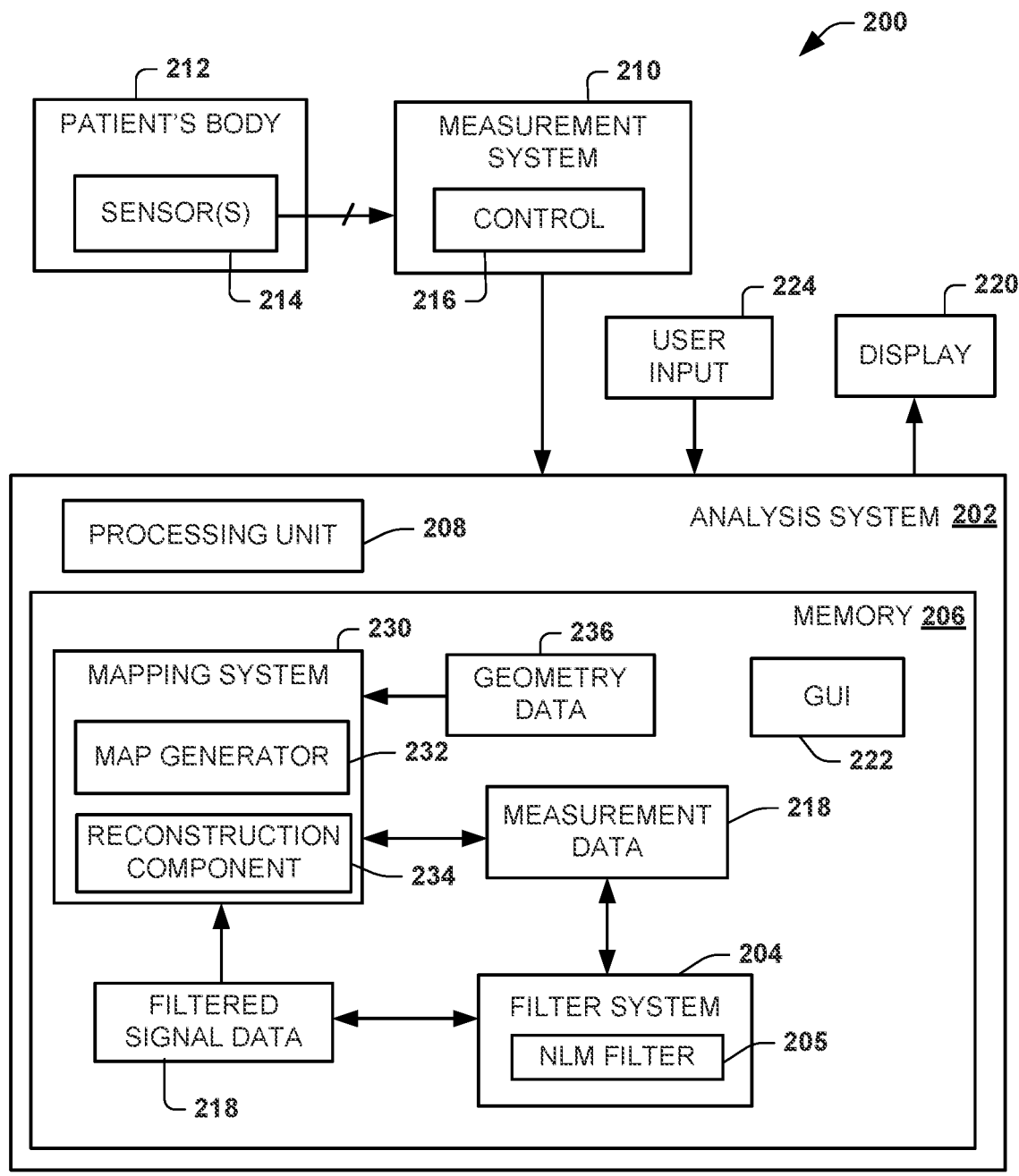
FIG. 6 depicts an example of a mapping system that can implement NLM filtering.

FIG. 6 depicts an example of an electrophysiological monitoring system 200 that can implement NLM filtering as disclosed herein. The system 200 can include an analysis system 202 that employs a filter system 204, as disclosed herein (e.g., corresponding to the filter system 10 of FIG. 1). The system filter system 204 can apply an NLM filter 205 in real time, such as during an electrophysiology study of a patient 212, or it can be implemented in relation to stored electrical measurement data previously acquired for a given patient. In some examples, the sensed electrical activity can be used to generate one or more graphical representations (e.g., graphical maps of electroanatomic activity) based on the sensed electrical activity, which can be provided to a display 220.

The analysis system 202 can be implemented as including a computer, such as a laptop computer, a desktop computer, a server, a tablet computer, a workstation or the like. The analysis system 202 can include memory 206 for storing data and machine-readable instructions. The memory 206 can be implemented, for example, as a non-transitory computer storage medium, such as volatile memory (e.g., random access memory), non-volatile memory (e.g., a hard disk drive, a solid-state drive, flash memory or the like) or a combination thereof. The instructions can be programmed to perform one or more methods, such as disclosed herein with respect to the examples of FIGS. 1, 2, 4 and 5.

The analysis system 202 can also include a processing unit 208 to access the memory 206 and execute the machine-readable instructions stored in the memory. The processing unit 208 could be implemented, for example, as one or more processor cores. In the present examples, although the components of the analysis system 202 are illustrated as being implemented on the same system, in other examples, the different components could be distributed across different systems and communicate, for example, over a network.

The system 200 can include a measurement system 210 to acquire electrophysiology information for a patient 212. In the example of FIG. 6, a sensor array 214 includes one or more electrodes that can be utilized for recording patient electrical activity. As one example, the sensor array 214 can correspond to an arrangement of body surface electrodes that are distributed over and around the patient's thorax for measuring electrical activity associated with the patient's heart (e.g., as part of an ECM procedure). In some examples, there can be about 200 or more sensors (e.g., about 252 sensors) in the array 214, each sensor corresponding to a node that defines a respective channel. An example of a non-invasive sensor array that can be used is shown and described in International application No. PCT/US2009/063803, which was filed 10 Nov. 2009, and is incorporated herein by reference. This non-invasive sensor array corresponds to one example of a full complement of sensors that can include one or more sensing zones. As another example, the sensor array 208 can include an application-specific arrangement of electrodes corresponding to a single sensing zone or multiple discrete sensing zones, such as disclosed in International application No. PCT/US2012/059957, which was filed 12 Oct. 2012, and is incorporated herein by reference. Additionally or alternatively, the sensor array 214 can include invasive sensors that can be inserted into the patient's body, such as via a catheter or other probe device.

The measurement system 210 receives sensed electrical signals from the corresponding sensor array 208. The measurement system 210 can include appropriate controls and signal processing circuitry (e.g., filters and safety circuitry) 216 for providing corresponding electrical measurement data 218 that describes electrical activity for each of a plurality of input channels detected by the sensors in the sensor array 214.

The measurement data 218 can be stored in the memory 206 as analog or digital information. Appropriate time stamps and channel identifiers can be utilized for indexing the respective measurement data 218 to facilitate the evaluation and analysis thereof. As an example, each of the sensors in the sensor array 214 can simultaneously sense body surface electrical activity and provide corresponding measurement data 218 for one or more user selected time intervals. Thus, the measurement data 218 can represent spatially and temporally consistent electrical information based on the where the sensors 214 are position on and/or in the patient's body 212.

The analysis system 202 is configured to process the electrical measurement data 218 and to generate one or more outputs. The output can be stored in the memory 206 and provided to a display 220 or other type of output device. As disclosed herein, the type of output and information presented can vary depending on, for example, application requirements of the user.

As mentioned, the analysis system 202 is programmed to employ NLM filter 205 to remove noise and/or transients from the measured electrical activity, which can results in improved accuracy in processing and analysis performed by the analysis system. The NLM filter 205 can, for example, be implemented to perform any one or combination of the filter functions disclosed herein (see, e.g., FIGS. 1, 2, 4 and 5 the corresponding descriptions). The NLM filter 205 thus can be applied to remove noise, transients or other signal features from signal stored in the memory as the measurement data 218. The filter system 204 can provide filtered signal data 218, including results from the NLM filter 205, that are stored in the memory 206, such as in conjunction with the measurement data 218 and other parameter data.

In some examples, the filter system 204 can interface with a graphical user interface (GUI) 222 stored as executable instructions in the memory 206. The GUI 222 thus can provide an interactive user interface, such as can be utilized to selectively configure one or more filter functions in response to a user input 224. The GUI 222 can provide data that can be rendered as interactive graphics on the display 220. For example, the GUI 222 can generate GUI elements (e.g., check boxes, radio buttons, sliding scales or the like) that a user can employ to activate or deactivate one or more filters for application to the input signal provided in the measurement data 218 and/or to configure parameters of the activated filter functions.

The analysis system 202 can also generate an output to be presented graphically on the display 220 representing filtered or unfiltered waveforms for one or more signals. As disclosed herein, the waveforms can represent filtered or unfiltered graphical representations of respective input channels, similar to waveforms demonstrated in FIG. 2, 3, 4 or 5. Alternatively, the output waveforms can represent filtered or unfiltered graphical representations of reconstructed waveforms, such as disclosed herein. In some examples, the graphical output of the waveform of selected signal(s) can be modified in substantially real time to reflect changes in the filters that have activated or deactivated and based on parameters that have been set in response the user input 224. In some examples, default values can be utilized for filter parameters unless modified in response to a user input 224, such as disclosed herein.

As a further example, the analysis system 202 can include a mapping system 230 that is programmed to generate electroanatomical map based on based on the filtered signal data. The mapping system 230 can include a map generator 232 that is programmed to generate map data representing a graphical (e.g., an electrical or electroanatomic map) based on the measurement data 218. The map generator 232 can generate the map data to visualize such map via the display 220 spatially superimposed on a graphical representation of an anatomical structure (e.g., the heart).

In some examples, the mapping system 230 includes a reconstruction component 234 programmed to reconstruct heart electrical activity by combining the measurement data 218 with geometry data 236 through an inverse calculation. The inverse calculation employs a transformation matrix and to reconstructs the electrical activity sensed by the sensor array 214 on the patient's body onto an anatomic envelope, such as an epicardial surface, an endocardial surface or other envelope. Examples of inverse algorithms that can be implemented by the reconstruction component 234 are disclosed in U.S. Pat. Nos. 7,983,743 and 6,772,004. The reconstruction component 234, for example, computes coefficients for a transfer matrix to determine heart electrical activity on a cardiac envelope based on the body surface electrical activity represented by the electrical measurement data 218. Since the reconstruction onto the envelope can be sensitive noise on the respective input channels, the filter system 204 helps to remove data for channels that would likely adversely affect the process.

The map generator 232 can employ the reconstructed electrical data computed via the inverse method to produce corresponding map of electrical activity. The map can represent electrical activity of the patient's heart on the display 220, such as corresponding to a map of reconstructed electrograms (e.g., a potential map). Alternatively or additionally, an analysis system 202 can compute other electrical characteristics from the reconstructed electrograms, such as an activation map, a repolarization map, a propagation map or other electrical characteristic that can be computed from the measurement data. The type of map can be set in response to the user input 224 via the GUI 222.

In view of the foregoing structural and functional description, those skilled in the art will appreciate that portions of the systems and method disclosed herein may be embodied as a method, data processing system, or computer program product such as a non-transitory computer readable medium. Accordingly, these portions of the approach disclosed herein may take the form of an entirely hardware embodiment, an entirely software embodiment (e.g., in a non-transitory machine readable medium), or an embodiment combining software and hardware. Furthermore, portions of the systems and method disclosed herein may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

What have been described above are examples. It is, of course, not possible to describe every conceivable combination of structures, components, or methods, but one of ordinary skill in the art will recognize that many further combinations and permutations are possible. Accordingly, the invention is intended to embrace all such alterations, modifications, and variations that fall within the scope of this application, including the appended claims.

Where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, and the term "including" means including but not limited to. The term "based on" means based at least in part on.

What is claimed is:

1. A non-transitory computer-readable medium having instructions executable by a processor, the instructions programmed to perform a method comprising:

applying a non-local mean filter to a given electrophysiological signal measured via at least one electrode from a patient thereby providing a first recovered signal and a first residual signal;

applying the non-local mean filter to one of the first recovered signal and the first residual signal and thereby providing a feature signal and a second residual signal; and combining the first recovered signal with the feature signal and thereby providing a filtered version of the given electrophysiological signal.

2. The medium of claim 1, wherein the non-local mean filter comprises a spatial domain filter to spatially weight the given electrophysiological signal relative to electrophysiological signals provided from neighboring electrodes according to spatial parameter data during the application of the non-local mean filter.

3. The medium of claim 2, wherein the non-local mean filter further comprises an intensity filter to weight based on a relative magnitude of a sample point of the given electrophysiological signal relative to corresponding sample points of the electrophysiological signals according to intensity parameter data during the application of the non-local mean filter.

4. The medium of claim 3, further comprising configuring the spatial parameter data and the intensity parameter data to be the same for each application of the non-local mean filter to the given electrophysiological signal.

5. The medium of claim 3, further comprising configuring the spatial parameter data and the intensity parameter data to be different for each application of the non-local mean filter to the given electrophysiological signal.

6. The medium of claim 3, further comprising configuring at least one of the spatial parameter data and the intensity parameter data in response to a control input.

7. The medium of claim 3, the method further comprising:
analyzing at least one of the first recovered signal and the first residual signal;
selectively configuring at least one of the spatial parameter data and the intensity parameter data based on the analyzing.

8. The medium of claim 1, wherein the given electrophysiological signal comprises one of a plurality of electrophysiological signals representing electrical activity associated with a geometric surface of patient tissue,
wherein each of the applying and the combining are performed with respect to at least a substantial portion of each of the plurality of electrophysiological signals.

9. The medium of claim 8, wherein each of the plurality of electrophysiological signals are derived at least one of invasively acquired electrical measurements for the patient or non-invasively acquired electrical data for the patient.

10. The medium of claim 1, further comprising:
identifying at least one transient feature in the given electrophysiological signal;
determining a time window associated with each identified transient feature; and
selectively applying filtering to at least one of the given electrophysiological signal, the first recovered signal and the first residual signal according to the determined time window and thereby removing each identified transient feature,
wherein selectively applying filtering further comprises one of applying the non-local mean filter configured for removal of transient features or applying a smoothing function.

11. The medium of claim 10,
wherein the non-local mean filter applied to the given electrophysiological signal is configured for denoising the given electrophysiological signal such that the first recovered signal comprises a denoised signal that includes the at least one transient feature; and
wherein selectively applying filtering is performed on the denoised signal.

12. The medium of claim 1, wherein the method further comprises generating a graphical output based on the filtered version of the given electrophysiological signal.

13. The medium of claim 1, wherein for a given application the non-local mean filter is configured according to a first set of filter parameters and for another application the non-local mean filter is configured according to a second set of filter parameters, wherein the first set of filter parameters is different from the second set of filter parameters.

14. A system comprising:
a plurality of sensors configured to measure electrophysiological signals from locations distributed across tissue associated with a patient;
memory configured to store machine readable instructions and the measured electrophysiological signals;
at least one processor configured to access the memory and configured to execute the machine readable instructions, the machine readable instructions comprising:
a non-local mean filter comprising a spatial filter and an intensity filter configured to adaptively average neighboring samples of the electrophysiological signals in a neighborhood for each sample of a given electrophysiological signal; and
a filter control configured to:
set spatial parameter data to configure the spatial filter according to a distance in a sampling space for the given electrophysiological signal, and
set intensity parameter data to configure weighting of the intensity filter according to an intensity difference between samples in the given electrophysiological signal.

15. The system of claim 14, wherein the filter control is further configured to apply the non-local mean filter to the given electrophysiological signal to provide a recovered signal and a residual signal, and wherein the system further comprises a signal analysis function configured to analyze at least one of the recovered signal and the residual signal, the filter control being further configured to set at least one of the spatial parameter data and the intensity parameter data based on the signal analysis.

16. The system of claim 15, wherein the signal analysis further comprises a spike detector configured to identify at least one transient feature in the given electrophysiological signal, the filter control to selectively apply filtering to the signal in a region of each identified transient feature in the given electrophysiological signal.

17. The system of claim 16, wherein the signal analysis further comprises a spatial region calculator configured to determine the region of each identified transient feature as a time window associated with each identified transient feature.

18. The system of claim 17, wherein the filter control is configured to selectively apply the filtering as one of the non-local mean filter configured to remove transient features or another filter function.

19. The system of claim 15, wherein the signal analysis further comprises a residual analysis function to analyze the residual signal, the filter control being further configured to control a number of iterations that the non-local mean filter is applied to the given electrophysiological signal based on the residual analysis function.

20. A system comprising:
memory to store machine readable instructions and store input electrical signal data representing at least a given electrophysiological signal acquired from a patient via a respective sensor; and
at least one processor to access the memory and execute the machine readable instructions configured to perform a method, the method comprising:

applying a non-local mean filter to the given electrophysiological signal, the non-local mean filter including a spatial filter that provides spatial filtering in a spatial domain of the given electrophysiological signal according to a distance between each sample and its neighboring samples of the given electrophysiological signal and an intensity filter to provide filtering in an intensity domain of the given electrophysiological signal according to an intensity difference between each sample and its neighboring samples of the given electrophysiological signal;

controlling parameters to establish weighting of each of the spatial filter and the intensity filter in response to a control input; and storing filtered signal data based on the applying and the controlling.

\* \* \* \* \*